United States Patent [19]

Bacquet et al.

[11] Patent Number: 4,550,075

[45] Date of Patent: Oct. 29, 1985

[54] METHOD FOR LIGAND DETERMINATION UTILIZING AN IMMUNOASSAY MONITORABLE BY BIOTIN-CONTAINING ENZYMES, AND COMPOSITIONS THEREFOR

[75] Inventors: Cathy A. Bacquet; Daniel Y. Twumasi, both of Austin, Tex.

[73] Assignee: Kallestad Laboratories, Inc., Austin, Tex.

[21] Appl. No.: 506,889

[22] Filed: Jun. 22, 1983

[51] Int. Cl.⁴ .................. G01N 33/54; C12Q 1/00; C12N 9/96
[52] U.S. Cl. ........................... 435/7; 435/4; 435/188; 435/810
[58] Field of Search ............ 435/7, 4, 188, 810; 436/501, 517, 518, 537, 805, 815

[56] References Cited

U.S. PATENT DOCUMENTS

| | | | |
|---|---|---|---|
| Re. 31,006 | 8/1982 | Schuurs et al. | 435/7 |
| 3,817,837 | 6/1974 | Rubenstein et al. | 195/103.5 R |
| 4,067,774 | 1/1978 | Rubenstein et al. | 195/63 |
| 4,134,792 | 1/1979 | Boguslaski et al. | 195/99 |
| 4,171,244 | 10/1979 | Blakemore et al. | 435/188 |
| 4,228,237 | 10/1980 | Hevey et al. | 436/518 |
| 4,233,402 | 11/1980 | Maggio et al. | 435/7 |
| 4,238,565 | 12/1980 | Hornby et al. | 435/7 |
| 4,273,866 | 6/1981 | Voss et al. | 435/7 |
| 4,496,654 | 1/1985 | Katz et al. | 435/7 |

FOREIGN PATENT DOCUMENTS

| | | | |
|---|---|---|---|
| 2754086 | 6/1978 | Fed. Rep. of Germany | 435/7 |
| 2023609A | 1/1979 | United Kingdom | 435/7 |
| 2018986A | 4/1979 | United Kingdom | 435/7 |
| 2019562A | 4/1979 | United Kingdom | 435/7 |
| 2023607A | 6/1979 | United Kingdom | 435/7 |
| 2043245A | 1/1980 | United Kingdom | 435/7 |
| 2098730 | 11/1982 | United Kingdom | 435/7 |

OTHER PUBLICATIONS

Henrikson et al., Analyt. Biochem., 94 (1979), 366–370.
Rappuoli et al., Analyt. Biochem., 118 (1981), 168–172.
Guesdon et al., Chem. Abstracts, 91 (1979), #119865e.
Applied Biochem & Biotech 7:443–454 (1982) Ngo et al.

Primary Examiner—Christine M. Nucker
Attorney, Agent, or Firm—Richards, Harris, Medlock & Andrews

[57] ABSTRACT

Methods and compositions are disclosed for the qualitative and quantitative identification of specific ligand in a fluid medium suspected of containing the ligand. The method of the present invention involves the formation of a liquid reaction mixture comprising an enzyme, a ligand-specific binding component, a conjugate comprising ligand coupled to a modulator label, and sample fluid medium suspected of containing ligand. Once the reaction mixture is formed, enzyme activity is monitored and the presence and amount of ligand in the sample fluid medium is determined by changes in enzyme activity.

Novel compositions useful in practicing the disclosed methods are provided. These include a biotin binding protein enzyme modulator, novel ligand-enzyme modulator conjugates, and biotin containing enzymes.

The methods and compositions of the present invention are particularly useful in the qualitative and quantitative identification of pharmaceuticals and any such antigenic units or sites, including haptens and fragments of large molecules present in such biologic fluids as blood, urine, spinal fluid, amniotic fluid, lymphatic fluid and the like.

26 Claims, No Drawings

METHOD FOR LIGAND DETERMINATION UTILIZING AN IMMUNOASSAY MONITORABLE BY BIOTIN-CONTAINING ENZYMES, AND COMPOSITIONS THEREFOR

TECHNICAL FIELD

This invention relates to assay methods wherein specific binding components are employed to qualitatively and quantitatively determine ligand in a sample fluid medium. More specifically, this invention relates to an immunoassay of the homogeneous or heterogeneous type employing non-radioisotopic label. In the preferred embodiment, this invention relates to an enzyme immunoassay system wherein the label is a biotin binding protein enzyme modulator monitored by changes in enzyme activity, the enzyme belonging to that class of biotin containing enzymes.

BACKGROUND ART

In medicine and clinical chemistry, immunoassay techniques are used for the qualitative and quantitative identification of various substances, hereinafter referred to as "ligands", in such body fluids as blood, urine, spinal fluid, amniotic fluid, lymphatic fluid, and the like. Examples of the classes of ligand identified by immunoassay techniques include pharmaceuticals, toxins, drugs of abuse, viral and bacterial antigens, hormones and immunoglobulins.

Most immunoassay techniques can be divided into two classes: radioimmunoassay (RIA) and enzyme immunoassay (EIA). RIA and EIA both depend on the competition between sample ligand, that substance suspected of being present in the fluid medium subjected to the assay, and labeled ligand, that same substance taken in a known amount and conjugated to a label or tag enabling one to follow the ligand. The RIA and EIA differ in the type of label employed. In the RIA, a radioisotope is conjugated to the ligand. In the conventional EIA, enzyme is conjugated to the ligand. Although radioisotopes are inherently more sensitive and less subject to serum interference than enzyme labels, several technical and economic factors favor the use of EIA over RIA. These include simplicity, speed, longer shelf life, less expensive instrumentation, avoidance of paperwork, waste disposal, and personnel training required for the use of radioactive materials.

During the past few years, many different EIA systems have been developed. These systems can be divided into two major types: heterogeneous EIA and homogeneous EIA.

Both types of EIA involve the formation of a reaction mixture comprising a minimum of three reaction components: a known amount of ligand, ligand-specific binding component, and sample fluid medium suspected of containing ligand. Heterogeneous EIA involves immobilization of one member of the ligand/ligand-specific binding component pair on solid phase and conjugation of the other member to an enzyme, the label. Typically, ligand is bound to enzyme to form an enzyme-ligand conjugate, the labeled ligand referred to above, and the ligand-specific binding component is immobilized on an insoluble solid phase. The labeled ligand in the enzyme-ligand conjugate then competes with sample ligand suspected to be present in the sample fluid medium for a limited number of ligand-specific binding sites. Once either labeled ligand or sample ligand is bound by the ligand-specific binding component, the bound ligand becomes insoluble. This competition occurs during an incubation step. The insoluble and liquid phases are then separated and the amount of enzyme in each phase quantitated. Sample ligand in the sample fluid medium is determined from the amount of enzyme bound to the solid phase following both these incubation and separation steps. The greater the amount of sample ligand in the sample fluid, the less the amount of enzyme will be found in the insoluble phase. Examples of heterogeneous binding reaction systems in which an enzyme is employed as the label component may be found in U.S. Pat. No. Re 31,006, *J. Immunol. Methods,* 1:247 (1972), and *J. Clin. Microbiol.* 3:604 (1976).

The early homogeneous EIA systems similarly employ an enzyme label but bring a simplicity of performance and ease of automation by eliminating the cumbersome separation and pre-incubation steps and by basing enzyme label monitoring on enzyme activity rather than an amount of enzyme bound. Examples of the homogeneous binding reaction systems in which an enzyme is employed as a label component may be found in U.S. Pat. Nos. 3,817,837 and 4,067,774. In these systems, as in the heterogeneous binding reaction systems, ligand is conjugated to enzymes. The formation of the enzyme-ligand conjugate, however, must not result in a change of enzyme activity, the ability of the enzyme to perform its normal catalytic functions. A change in enzyme activity must only occur upon the subsequent binding of the enzyme-ligand conjugate by the ligand-specific binding component. This change in enzyme activity may be an inhibition or stimulation of normal enzyme activity. The presence and quantitation of ligand in the sample fluid is determined by the ability of the sample fluid to protect enzyme activity from the effects of the ligand-specific binding component. Protection is effectuated by the competition between sample and conjugated ligand for ligand-specific binding component binding.

The required retention of enzyme activity following enzyme-ligand conjugation in the enzyme-label systems is, in practice, often difficult to achieve. The heterologous and labile nature of enzymes create problems in characterizing, stabilizing and reproducibly preparing enzyme-ligand conjugates. Additionally, the mandated retention of enzyme activity following ligand-enzyme conjugation restricts the molecular size of the ligand which may be conjugated to enzyme. The size limitation is, in most instances, a stearic one. Ligand must not be so large as to stearically inhibit enzyme activity. These problems have been overcome, to some extent, by replacing the enzyme label with low molecular weight labels monitorable by their respective affects on enzyme activity. These low molecular weight labels, referred to as modulator labels, include prosthetic groups, coenzymes, enzyme substrates, and enzyme modulators. Examples may be found in U.S. Pat. No. 4,238,565; GB Pat. No. 2,023,609A; U.S. Pat. Nos. 4,134,792 and 4,273,866, respectively. The use of the low molecular weight, less than 500 molecular weight, modulator labels, however, has retained the molecular size limitation on the ligands which may be assayed in these systems. As with the enzyme labels, ligand must not be so large as to stearically inhibit the activity of the modulator label to which ligand is conjugated. Thus, the types of ligands assayable in present systems are limited to a molecular size in keeping with the label employed in the assay.

The novel large molecular weight protein label employed in the present invention should greatly expand the molecular size range of ligands which may be assayed for in an EIA. Additionally, since the large molecular weight protein label employed in the present invention is a modulator label, this novel label retains those advantages of other modulator labels such as stability, ease of conjugation and the like. The novel label employed in the present invention is the large molecular weight, biotin-binding, natural inhibitor of pyruvate carboxylase, avidin. Avidin has previously been employed as a ligand-specific binding protein for determination of free biotin in sample fluids. Examples are found in U.S. Pat. No. 4,134,792 and *Applied Biochem. & Biotech.*, 7:443–54 (1982). The novel employment of avidin as a modulator label in the present invention brings with it several advantages inherent in the avidin molecule itself, such as, molecular stability, ease of conjugation, standardization and high yield in conjugate formation.

The present invention also employs a novel use for that class of biotin-containing enzymes of which the preferred enzyme is pyruvate carboxylase. Pyruvate carboxylase is extremely stable, highly active and easily monitored with standard clinical laboratory equipment.

Additionally, pyruvate carboxylase is not present in significant amounts in normal human body fluids such fluids being subjected to the method of the present invention. Thus, unlike some existing EIA systems, pyruvate carboxylase does not cause levels of background interference which must be specifically corrected for.

In a further aspect, the present invention employs a novel enzyme/enzyme modulator combination. The novel combination of biotin-containing enzymes with large molecular weight, biotin-binding enzyme modulators in the present invention provides a novel ligand specific binding assay of the homogeneous or heterogeneous type with enhanced sensitivity, diminished interference, versatility and simplicity of instrumentation.

SUMMARY OF THE INVENTION

This invention encompasses a metnod for the qualitative and quantitative identification of a specific ligand in a fluid medium suspected of containing said ligand. The method of the present invention comprises formation of a liquid reaction mixture with reaction components comprising: an enzyme, a ligand-specific binding component, a conjugate comprising ligand coupled to a modulator label, and sample fluid medium suspected of containing ligand. Once the reaction mixture is formed, enzyme activity is monitored and the amount of ligand present in the sample fluid medium is determined by changes in enzyme activity.

In another aspect, the present invention provides novel enzyme modulators, ligand-enzyme modulator conjugates, and biotin containing enzymes useful as reaction components in practicing the above method.

Methods and components of the present invention are particularly useful in the qualitative and quantitative identification of pharmaceuticals and any such antigenic units or sites, including haptens and fragments of large molecules present in such biologic fluids as blood, urine, spinal fluid, amniotic fluid, lymphatic fluid and the like.

DETAILED DESCRIPTION OF THE INVENTION

The present invention relates to methods and compositions for determining ligands in fluid mediums suspected of containing said ligands.

In the context of this disclosure, the following terms shall be defined as follows unless otherwise stated:

"ligand" is a substance whose presence or amount thereof, in a sample fluid medium, is to be determined;

"ligand-specific binding component" is any substance, or group of substances, which have a specific binding affinity for the ligand to be assayed therefor;

"ligand analogue" is any substance, or group of substances containing a site or sites which will be recognized and bound by the ligand-specific binding component to the exclusion of other substances except ligand itself;

"label" is any substance, or group of substances, which is either directly or indirectly involved in the production of a detectable signal and may be bonded to ligand, ligand analog, or ligand-specific binding component;

"labeled conjugate" is the resultant substance formed by the coupling of label to ligand, ligand analog or ligand-specific binding component;

"monitoring enzyme" is that enzyme whose activity is either stimulated or inhibited by the label and whose change in activity determines the presence or amount of ligand in the fluid medium.

Fluid mediums particularly suited to the method in this invention are body fluids such as blood, urine, spinal fluid, amniotic fluid, lymphatic fluid and the like.

The method of the present invention, involves a ligand specific binding reaction of the homogenous or heterogeneous type in which the presence and amount of ligand is determined by changes in enzyme activity. A reaction mixture comprising the monitoring enzyme, ligand-specific binding component, labeled conjugate and sample fluid medium suspected of containing ligand is formed. The labeled conjugate comprises a known amount of ligand coupled to an enzyme modulator wherein said labeled conjugate is capable of modulating the activity of the monitoring enzyme. Modulation includes enzyme inhibition or stimulation and is monitored by measuring enzyme activity. The ability of the labeled conjugate to modulate enzyme activity is abolished when sufficient amounts of ligand-specific binding component are present in the reaction mixture due to binding of the labeled conjugate by the ligand-specific binding component. Only when ligand is present in the sample fluid medium and said fluid medium is added to the reaction mixture is the modulator activity of the labeled conjugate restored. Sample ligand competes with the ligand in the labeled conjugate for ligand-specific binding component binding to prevent the latter component from binding to and thus abolishing the modulating activity of the labeled conjugate. The activity of the monitoring enzyme therefore becomes a direct measure of ligand presence and amount in the sample fluid medium.

Representative ligands determinable by the methods and compositions of the present invention include pharmaceuticals, toxins, drugs of abuse, hormones, immunoglobulins and any antigenic substance or unit thereof to which a ligand-specific binding component naturally exists or may be generated. Ligands may be assayed for as specific substances for example an assay for dilantin, a specific anti-convulsant, or for a class of substances such as the gamma class of immunoglobulins. Methods and compositions are provided for determining dilantin, theophylline and lidocaine in sample fluids. The presence of dilantin in sample fluids is determined at levels equivalent to therapeutic concentrations, 10–20 micrograms per milliliter.

Ligand-specific binding components include naturally existing receptors or binding proteins and those substances which may be generated synthetically or biologically. An example of a biologically generated ligand-specific binding component is antibody. In the preferred embodiment of the present invention, ligand-specific antibody of the multivalent or monoclonal type is provided and employed as ligand-specific binding component.

Ligand analogs include derivatives, homologues or such molecules or antigenic fragments thereof containing the site or sites recognized and bound by ligand-specific binding components. Typically, ligand analogs may be created by modifying ligand molecules to ligand-esters, acids, amides, amines, and hydroxy forms which retain the critical binding regions of the ligand molecule recognized by the ligand-specific binding component.

The monitoring enzyme provided for and employed in the present invention is a biotin-containing enzyme whose activity is inhibited by the enzyme modulator. Representative biotin-containing enzymes include pyruvate carboxylase, transcarboxylase, acetyl coenzyme A carboxylase, propionyl coenzyme A carboxylase and any enzyme which naturally contains or is modified so as to contain a biotin moiety. Of these biotin-containing enzymes, the preferred enzyme is pyruvate carboxylase.

Pyruvate carboxylase is a very stable and highly active enzyme. The high activity of pyruvate carboxylase, turnover number of 6000 at 37° C. in the citrate synthese coupled reaction, provides a very sensitive means for determining ligand in fluid mediums as slight changes in activity can be easily detected and quantitated. Furthermore, the concentration of free biotin and biotin-containing enzymes in such body fluids as serum is not high enough to significantly interfere with the assay. The assay method of the present invention is therefore essentially free from possible competition or interference from fluid medium components.

Pyruvate carboxylase catalyzes the conversion of pyruvate to oxaloacetate and the hydrolysis of ATP. The enzyme contains four biotin molecules covalently linked to specific lysine residues at active sites on each of four subunits. The biotin serves as an intermediate carrier for the carboxyl group which is transferred to pyruvate to form oxaloacetate. Acetyl coenzyme A(acetyl CoA) is an allosteric activator of the enzyme from vertebrates and some bacteria.

In order to monitor enzyme activity, the pyruvate carboxylase reaction is coupled to either citrate synthase or malate dehydrogenase reactions. Citrate synthase produces citrate from oxaloacetate and converts acetyl CoA to coenzyme A. Coenzyme A reduces the disulfide of Ellman's reagent which causes an increase in absorbance at 412 nm. Malate dehydrogenase catalyzes the reduction of oxaloacetate to malate which results in the conversion of NADH to NAD+ and a subsequent decrease in absorbance at 340 nm. The spectrophotometric monitoring of enzyme activity provides a simplicity of instrumentation and economic adaptability to clinical laboratories as such laboratories are normally equipped with such instrumentation means. Some serum interference in the malate dehydrogenase coupled system is noted in individuals with elevated lactate dehydrogenase (LDH) as LDH also produces NAD+ in the presence of the substrate pyruvate. Elevated LDH concentrations in serum is a common symptom in conditions such as jaundice, anemia, carcinoma and myocardial infarcts. Interference may be correct for by using patient serum in assay controls in the citrate synthase reaction.

Labeling substances in the present invention include protein enzyme modulators. Unlike present low molecular weight modulators which are generally of a molecular weight less than around 500, protein modulators have a molecular weight generally in excess of 10,000. The method of the present invention employs such large molecular weight, biotin-binding, protein enzyme modulators as avidin, molecular weight around 68,000, anti-biotin antibodies, molecular weight around 150,000–160,000, or any such biotin-binding component. The preferred label is the enzyme modulator avidin, the natural inhibitor of pyruvate carboxylase.

The novel employment of avidin as the label in the present method has several advantages over previous labels. Avidin is extremely stable. Avidin retains its ability to bind biotin in a pH range of 2 to 13, at temperatures up to 85° C. and binding is resistant to proteolysis with trypsin and pronase. Additionally, conjugation of ligand to avidin, to create the labeled conjugate, is standardized in the present method and results in a high yield of conjugate formation. Conjugation is achieved by a standard acylation and addition reactions. Furthermore, the large molecular size of avidin should allow for the conjugation of a wide molecular size range of ligand molecules without resultant loss of enzyme modulator activity. Previous systems are severely limited in the size of ligand that may be conjugated to either the enzyme-label or low molecular weight prothetic group, coenzyme, enzyme substrate and enzyme modulator-labels. The small size of the latter labels, less than 500, and lability of the enzyme-labels prohibit the conjugation of large molecular weight ligands without resultant loss in the activity of the label component, such activity being the critical focus of the assay. An additional advantage of the present method, is the molecular interaction between avidin and the biotin-containing enzymes. Tie avidin-enzyme interaction yields a highly sensitive and precise means for determining ligand in a fluid medium. Avidin has an extremely high affinity, around $10^{15}$ molar $^{-1}$, for biotin alone and, around $10^{12}$ molar $^{-1}$, for biotin moieties of enzymes. The resultant non-covalent binding is essentially irreversible. This high binding affinity allows for the inhibition of theoretically all enzyme activity and, in practice, protects against displacement and interference from both enzyme substrates and potentially interfering substances present in the fluid mediums assayed.

To form the novel labeled conjugate which participate in the assay methods, the enzyme modulator is covalently linked to the ligand to be detected, ligand analog, or a ligand-specific binding component. The choice of components in the labeled conjugate is determined by the assay method selected. These assay methods will be described in detail hereinafter. The method employed to link or couple the components in the labeled conjugate is important only in so far as the resulting enzyme modulator component of the labeled conjugate retains a measurable amount of modulating activity, that the ligand and ligand analogue components retain their respective abilities to be specifically bound by the ligand-specific binding component, and that the ligand-specific binding component retains its ability to bind ligand or ligand analogue. In general, the enzyme modulator and binding component are linked directly or by a chain bridge group having active coupling groups at opposite ends that bind the respective moieties to be linked. The methods used to link the components of the labeled conjugate are known in the art such as those described in *Res. Commun. Chem. Path. Pharmacol.* 13: 497 (1976); *Proc. Soc. Exp. Biol. Med.* 98:898 (1958); *J. Am. Chem. Soc.* 88:1338 (1966), incorporated by reference herein.

In the preferred embodiment, the labeled conjugate comprises ligand coupled to the enzyme modulator, avidin. Formation of the labeled conjugate does not interfere with avidin's ability to modulate, inhibit, the enzyme activity of the preferred enzyme, pyruvate carboxylase. Only upon the addition of ligand-specific binding component, is the inhibitory activity of the labeled conjugate abolished.

The compositions provided for in the present invention are useful in several of the assay methods described in the following examples. In each of the methods described, enzyme modulator is coupled to ligand to form the labeled conjugate. It is understood that the enzyme modulator may also be coupled to ligand analog or ligand-specific binding component to form the labeled conjugate in these and other assay methods. Ligand is determined by measuring the enzyme activity of the monitoring enzyme.

For purposes of illustration only, the following are examples of several assay methods based on homogeneous and heterogeneous competitive binding techniques whereas it will be understood that other homogeneous and heterogeneous techniques can be followed in practice.

In an example of the homogeneous scheme, ligand is conjugated to the enzyme modulator in a liquid medium. The resultant labeled conjugate retains the modulator's ability to inhibit enzyme activity. The subsequent addition of a ligand-specific binding component blocks the ability of the labeled conjugate to inhibit the enzyme. When ligand is present in the fluid medium to be assayed, and the fluid medium is added to the assay mixture, ligand will compete with the ligand component of the labeled conjugate for binding of the ligand-specific binding component and prevent the ligand-specific component from binding the labeled conjugate and thus restore the inhibitory capabilities of the labeled conjugate. In such a case, the amount of enzyme inhibition restored in the system is directly related to the amount of ligand present in the fluid medium assayed.

In an example of the heterogeneous scheme, the ligand-specific binding component is linked to a matrix to create an insoluble phase. The ligand-specific binding component is linked in such a manner as to retain the ligand-specific binding component's ability to bind the ligand or ligand analog component of the labeled conjugate. The insoluble phase is then mixed with soluble labeled conjugate and fluid medium suspected of containing ligand in a liquid phase. When ligand is present in the fluid medium, ligand will compete for binding by the ligand-specific binding component with the labeled conjugate. The insoluble phase is then separated from the mixture and the resultant liquid medium assayed for ability to inhibit enzyme. When ligand is present in the fluid medium, the labeled conjugate or some portion thereof will remain in the liquid and retain its ability to inhibit enzyme. The amount of enzyme activity inhibited by the liquid phase will directly indicate the amount of ligand present in the fluid medium.

The inventors believe that an alternate method can be employed. This assay is a type of homogeneous-heterogeneous hybrid. The solo term "heterogeneous" does not seem appropriate as separation steps are not required. Yet, a solid phase is employed and hence the term hybrid. In an example of this hybrid system, labeled conjugates are preabsorbed to such surfaces as microtiter wells or tubes. Fluid medium suspected of containing ligand is then added to the tube or well to which conjugate has been preabsorbed. Ligand-specific binding component and the monitoring enzyme are simultaneously added. The assay components are allowed to incubate for a period of time, for example 10 minutes, after which period enzyme substrates are added and enzyme activity quantitated. The presence or amount of ligand in the fluid medium assayed is directly related to amount of enzyme activity inhibited. It is anticipated that this hybrid system may be varied by preabsorbing different assay components such as enzyme or ligand-specific binding component alone or in combination.

Known variations of the above briefly described homogeneous and heterogeneous methods and further details concerning specific techniques discussed are readily available in the literature e.g. U.S. Pat. No. 3,817,837 and U.S. Pat. No. Re. 31,006, respectively; *J. Clin. Microbiol.*, 3:604 (1976); *J. Immunol. Methods*, 20:365 (1978).

EXAMPLE 1

Preparation of Assay Components

A. Pyruvate Carboxylase

The biotin containing enzyme, pyruvate carboxylase, was isolated from two distinct species and genera of bacteria, *Pseudomonas citronellolis* and *Bacillus stearothermophilus*.

1. Isolation and Purification of Pyruvate Carboxylase from *B. stearothermophilus*.

A frozen cell paste (45 g) was thawed at 4° C. and resuspended in 200 ml of buffer containing 50 mM Tris-Cl, pH 7.6, 1 mM EDTA, and 150 mM KCl (Buffer 3). Sixty µg of lysozyme per ml of cell suspension were added. The cell suspension was incubated for 30 minutes in a 37° C. water bath. An equal volume of Buffer 3 (with no KCl) was then added.

All subsequent steps were performed at 4° C. unless otherwise specified. The cell cytosol was separated by ultracentrifugation at 148,000×g for 35 minutes in a Beckman Model L5-75B with a 70Ti rotor. Twenty-five ml of a 2% protamine sulfate solution was added dropwise to the pooled supernatant. The solution was slowly stirred for 10 minutes. The suspension was centrifugated at 22,000×g for 40 minutes. Solid $(NH_4)_2SO_4$ was slowly added to the supernatant with constant stirring. After 4 hours, the precipitated protein was pelleted by centrifugation at 22,000×g for 30 minutes. The precipitate was resuspended in Buffer 4 comprising 0.1M Tris-HCl, pH 7.5, containing 0.5M KCl, 1 mM EDTA, 0.1 mM dithiothreitol (DTT) and 5% glycerol. Viscosity of the solution was reduced with the addition of 425 µg of DNase and incubation in a 30° C. water bath for 30 minutes. The solution was dialyzed overnight against Buffer 4.

A monomeric avidin affinity column (2×18.5 cm) was prepared as per the method in *Anal. Biochem.* 94, 366 (1979) as modified in *Arch. Biochem. Biophys.* 201, 669 (1980). The dialyzed partially purified enzyme was centrifuged to remove any precipitate and then loaded onto the monomeric avidin affinity column. The column was washed with Buffer 4 until the absorbance at 280 nm was zero. Then, a 500 μl linear gradient of biotin (0–60 μM) in Buffer 4 was applied to the column. All fractions were assayed for enzyme activity and active fractions from the buffer wash and gradient were pooled separately. Protein loss was reduced and stability increased by addition of 10 mg per ml bovine serum albumin (BSA) to the pooled fractions from the gradient.

Avidin contamination from the column was eliminated from the pooled fractions by dialysis in membrane with a molecular weight cut-off of 50,000. The dialysis buffer consisted of 50 mM Tris-HCl, pH 7.5, 5 μM acetyl CoA, 0.1 mM ATP, 0.1 mM $MgCl_2$, 0.1 μM $ZnSO_4$ and 0.02% sodium azide.

The enzyme solution was stored at 4° C. Some of the solution was divided into small samples, lyophilized, and stored at room temperature to determine stability.

2. Isolation and Purification of Pyruvate Carboxylase from *P. Citronellolis*.

A lyophilized culture of *P. citronellolis* was purchased from the American Type Culture Collection and stored frozen at −50° C. in double strength skim milk. *P. citronellolis* was subcultured monthly on 1% tryptone-agar slants.

Precultures of *P. citronellolis* (500 ml.) were grown in 2 l. Erlenmeyer flasks at 30° C. on a rotary shaker at 150 rpm. A preculture was used to inoculate 12 l. of growth medium in a New Brunswick fermentor. A growth medium, described in *J. Biol. Chem.* 254:9262 (1979), containing lactate as a source of carbon was employed.

Cells were harvested in late logarithmic phase by continuous flow of centrifugation, using a Sharples centrifuge. The cells were weighed and washed with Buffer 1 containing 0.1M potassium phosphate buffer, pH 7.2, 5 mM EDTA, 1 mM $MgCl_2$, 0.1 mM DTT, and 0.1 mM phenylmethylsulfonylfluoride (PMSF).

All purification steps were performed at 4° C. Cells were diluted 2 to 1 with Buffer 1 and subjected to two passages through a French pressure cell at 7–8,000 psi. Cell debris was removed by centrifugation at 22,000×g. The resultant cell extract was stored at −50° C.

A partial purification of the enzyme was developed to decrease lactate dehydrogenase contamination in assay measurements. Saturated $(NH_4)_2SO_4$ was slowly added to cell extract to 50% saturation with constant stirring. After centrifugation at 22,000×g, the resulting precipitate was dissolved in 0.02M imidazole, pH 7.0, 0.4M $(NH_4)_2SO_4$, 0.2 mM DTT. The material was then loaded on a Sephadex G-200 column (2.5×78 cm) and equilibrated with the same buffer. The fractions of the first peak, which had pyruvate carboxylase activity, were pooled and concentrated by addition of saturated $(NH_4)_2SO_4$ solution to 50%. The precipitated protein was divided and resuspended in one of three buffers. Buffer A consisted of 0.1M potassium phosphate, pH 7.2, and 1.5M sucrose. Buffer B contained 0.02M imidazole, pH 8.0, and 0.4M $(NH_4)_2SO_4$. Buffer C contained 0.02M imidazole, pH 8.0, and 4.2M $(NH_4)_2SO_4$. All three buffers contained 0.2 mM DTT, 1 mM EDTA, 0.1 mM PMSF, and 500 Kallikrein units/ml of aprotinin that had been filter-sterilized. The enzyme solutions were stored at 50 μl fractions at −50° C., −4° C., and in liquid and lyophilized forms at 23° C. The enzyme solutions were also stored in plastic viles in liquid nitrogen.

Pyruvate carboxylase was affinity purified from *P. citronellolis* cell extract as described in the previous section for *B. stearothermophilus* with the following buffer modifications. Protein concentration of the protamine sulfate-treated cell extract was performed by addition of saturated $(NH_4)_2SO_4$ in 0.1M potassium phosphate buffer, pH 7.2, 1 mM EDTA, 0.2 mM DTT, 0.1 mM PMSF. In the affinity chromatography, Buffer 4 contained 0.4M $(NH_4)_2SO_4$ instead of 0.5M KCl. The pooled enzyme fractions were concentrated by additions of $(NH_4)_2SO_4$ or by vacuum dialysis. The concentrated enzyme was diluted in one of the three following buffers: Buffer A as described, Buffer A containing 10 mg/ml BSA, or Buffer A containing BSA and 0.02% sodium azide. The solutions were stored at −50° C.

B. Preparation and Maintenance of Monomeric Avidin

Monomeric avidin was prepared from 80 ml of immobilized avidin crosslinked to 6% beaded agarose as described by Henrikson et al., *Anal. Biochem.* 94:366 (1979), as modified by Gravel et al., *Arch. Biochem. Biophys.* 201:669 (1980). The immobilized avidin was poured into a column (2×18.5 cm) and washed with 0.25M sodium acetate, pH 5.5, until the absorbance at 280 nm was zero. Denatured avidin was eluted from the column with 6M guanidine-Cl in 0.2M KCl-HCl, pH 5.1. The agarose remained in this buffer overnight in the column. It was then washed with the same buffer until no protein was detected in the eluant. The column was transferred to 4° C. and equilibrated in Buffer 4.

Any tetrameric avidin with high affinity for biotin remaining on the column was blocked with 500 ml of 0.8 mM biotin in Buffer 4. Biotin bound to low affinity monomeric avidin was eluted with one liter of 0.1M glycine-HCl, pH 2.0. The column was then re-equilibrated with Buffer 4.

After elution of biotin-containing enzymes, the column was washed with one liter of 0.1M glycine-HCl, pH 2.0, 500 ml of Buffer 4, 500 ml of 0.8 mM biotin in Buffer 4, and one liter of 0.1M glycine-HCl, pH 2.0.

C. Ligand—Avidin Conjugate Formation

1. Conjugation of DPH to Avidin

A 2.0 mg/ml solution of avidin was dialyzed against 0.16M borate buffer (pH 7.9) and 0.134M NaCl (Buffer 5). After dialysis, the avidin solution was titrated with 0.01M 4'-hydroxyazobenzene-2-carboxylic acid (HABA) at 500 nm. Two milliliter portions were placed in 4 ml screwcap stirrer vials and chilled in an ice bath. [$N^3$-(5,5-diphenyl-hydantoin)]-acetic acid-(N-hydroxysuccinimidyl ester) (DPH ester) was dissolved in dimethylacetimide (DMA) as a 5 mg/ml solution. One hundred microliters were added slowly to the avidin solution with constant stirring at 4° C. The solution was stirred at 4° C. for 15 minutes and at 23° C. for 30 minutes. The solution was filtered and then eluted through a Sephadex G-25 column equilibrated with Buffer 5. Eluted protein was pooled and stored in a 0.02% azide solution at 4° C. Use of molar ratios of DPH ester to avidin in the range of 2.63 to 21.0 produce yields of 88–100% conjugate formation.

The conjugation occurs as follows:

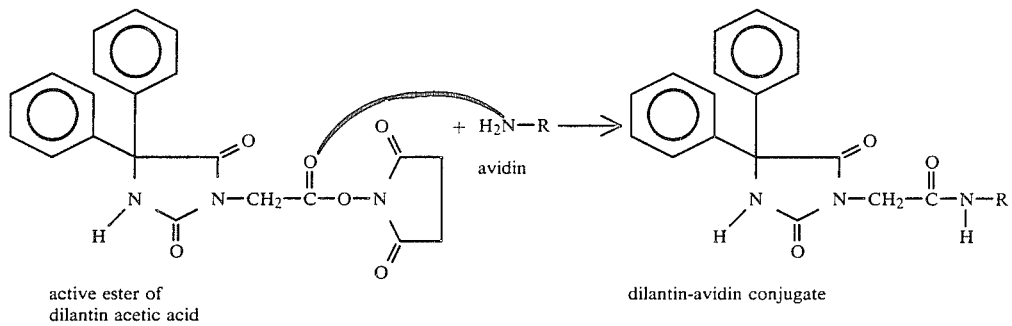

active ester of dilantin acetic acid dilantin-avidin conjugate

The optimum ratio of DPH to avidin in the labeled conjugate is between 6 and 10. The ratio of DPH to avidin may be decreased by reduction of the DPH ester from 10 mg/ml to 5.0, 2.5, 1.25, and 0.625. In each synthesis, the solution was stirred for 30 minutes at 23° C.

The ratio of DPH to avidin was estimated by the reaction of 2, 4, 6-trinitrobenzene-sulfonic acid (TNBS) to the free amines of avidin and DPH-avidin conjugates. Twenty-five to two hundred micrograms of protein was diluted in 0.5 ml of Buffer 5 and 0.5 ml of 0.1M borate buffer, pH 9.3. Twenty-five microliters of 0.2M TNBS were added. The absorbance at 420 nm was measured after 30 minutes. The extinction coefficient is $20 \times 10^3 M^{-1} cm^{-1}$.

2. Conjugation of Lidocaine to Avidin

Five milligrams of avidin per milliliter was dialyzed against 0.1M $KHCO_3$, pH 8.4. The solution was titrated with 0.01M HABA. Next, 0.625 mg of lidocaine, isothiocyanate in 50 μl of dimethylacetimide was added as a suspension to the avidin solution (25 molar ratio in solution). The solution was stirred for 4 hours at room temperature. The reaction mixture was then elerted through a Sephadex G-25 column in Buffer 5. Eluted protein was pooled and stored in a 0.02% azide solution at 4° C.

The conjugation occurs as follows:

lactam of carboxypropyltheophylline theophylline-avidin conjugate

D. Ligand-Specific Binding Components

Polyclonal antisera and/or monoclonal antibody to

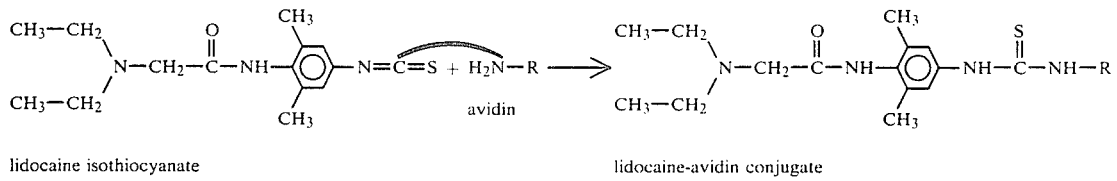

lidocaine isothiocyanate lidocaine-avidin conjugate

3. Conjugation of Theophylline to Avidin

Ten milligrams of avidin were dialyzed in 5 ml against borate buffer, pH 8.0. Two milliliters of dialysate were placed in a stirrer vial and titrated against 0.01M HABA. Fifty milligrams of the lactam of carboxypropyl theophylline was dissolved in 5 ml of dimethylacetimide (95 molar ratio in reaction). On hundred microliters of the lactam was added in 50 μl aliquots to the stirrer vial and the solution was stirred at 4° C. for 20 minutes and at room temperature for 30 minutes. The solution was eluted through a Sephadex G-25 column in borate buffer. Eluted protein was pooled and stored in a 0.02% azide solution at 4° C.

The conjugation occurs as follows:

such haptens as dilantin, lidocaine and theophylline were prepared by standard techniques. Polyclonal antisera to haptens were generated in animals, such as rabbits or goats by serial immunization with hapten-macromolecular conjugates. For example, dilantin was conjugated to keyhole limpet hemocyanin. Goats were immunized once a week for a period of four weeks then boosted twice a month during the period of antisera collection. Monoclonal antibody to lidocaine was prepared in accordance with the methods described by Kohler and Milstein in *Nature* 256:495 (1975) incorporated by reference herein.

EXAMPLE 2

Pyruvate Carboxylase Monitoring Assay

All enzyme assays were performed in one ml quartz cuvettes or an aspirating microcuvette, model 3018A, using a Gilford UV-VIS Microprocessor-Controlled Spectrophotometer System 2600. All reactions were initiated by the addition of pyruvate carboxylase. Assays were performed at room temperature (23° C.) or at 37° C. achieved by circulation of heated water through the cuvette block and incubation of reaction components in a 37° C. water bath.

A. *P. citronellolis* Pyruvate Carboxylase

Pyruvate carboxylase activity in crude extracts of *P. citronellolis* was measured using an assay coupled to a reaction catalyzed by citrate synthase. The reaction was monitored by the increase in absorbance at 412 nm due to reduction of 5-5' dithiobis (2-nitrobenzoic-acid) (DTNB) by coenzyme A. The components of the 1 ml assay include: 100 μmoles of N-2-hydroxyethyl pipirazine-N'-2-ethane sulfonic acid (HEPES), pH 7.6, 2 μmoles ATP, 10 μmoles pyruvate, 5 μmoles $MgCl_2$, 10 μmoles KCl, 15 μmoles $NaHCO_3$, 0.25 μmoles EDTA, 0.1 μmoles DTNB, 0.15 μmoles acetyl CoA, and 1.0 unit of citrate synthase.

Purified enzyme preparations were assayed with a coupled malate dehydrogenase assay. One-half unit of malate dehydrogenase and 0.2 μmoles NADH replaced DTNB, acetyl CoA, and citrate syntase in the assay mixture described above. Oxidation of NADH was monitored by the decrease in absorbance at 340 nm.

B. *B. stearothermophilus* Pyruvate Carboxylase

When pyruvate carboxylase from *B. stearothermophilus* was assayed, the reaction was coupled to either citrate synthase or malate dehydrogenase. The 1 ml reaction mixture consisted of 100 μmoles Tris-Cl, pH 8.0, 5 μmoles $MgCl_2$, 100 μmoles $KHCO_3$, 3.3 μmoles sodium pyruvate, 0.1 μmoles acetyl CoA, 1.67 μmoles ATP, 0.1 μmoles DTNB, and 1 unit citrate synthase. When the assay was coupled to the malate dehydrogenase reaction, DTNB and citrate synthase were replaced with 0.22 μmoles NADH and 0.5 unit malate dehydrogenase.

EXAMPLE 3

Homogeneous Binding Assay for DPH

Twenty-five microliters (0.55 μg) of pyruvate carboxylase (P.C.), prepared as described in part A of Example 1, was diluted with 20 μl of goat anti-DPH antibody (GXDPH), prepared as described in part D of Example 1, 60 μl ( b12 μg) of DPH-avidin conjugate, prepared as described in part C of Example 1, and 95 μl of DPH containing various μg amounts of DPH to a volume of 200 μl and then diluted to 1.0 ml with substrates as indicated in Table 1. The 200 μl reaction mixture was allowed to incubate for 10 minutes at 23° C. prior to the addition of substrates when the reaction was run at 23° C. No pre-incubation of the 200 μl reaction was required when assay components were equilibrated in a 37° C. water bath. The rate or change in absorbance at 412 nm per minute (ΔA) was measured at 23° C. or 37° C. The reactions set forth in Table 1 were conducted at 37° C. The rate (ΔA) was subtracted from the rate of the control (ΔA°) which contained all the assay components except DPH.

TABLE 1

| Rxn No. | P.C. (0.55 μg) | DPH-Avidin (12 μg) | GXDPH (20 μl) | DPH (μg) | ΔA | (ΔA°-ΔA) × 100 |
|---|---|---|---|---|---|---|
| 1 | + | + | — | — | 0.0552 | — |
| 2 | + | + | + | — | 0.1605 | 0 |
| 3 | + | + | + | 0.0098 | 0.1584 | 0.22 |
| 4 | + | + | + | 0.0195 | 0.1584 | 0.24 |
| 5 | + | + | + | 0.039 | 0.1525 | 0.80 |
| 6 | + | + | + | 0.078 | 0.1451 | 1.55 |
| 7 | + | + | + | 0.156 | 0.1326 | 2.80 |
| 8 | + | + | + | 0.313 | 0.1223 | 3.83 |
| 9 | + | + | + | 0.625 | 0.1130 | 4.76 |
| 10 | + | + | + | 1.25 | 0.1070 | 5.36 |
| 11 | + | + | + | 2.50 | 0.0952 | 6.54 |

The results in Table 1 indicate that DPH can be conjugated to avidin to form a labeled conjugate without destroying avidin's ability to inhibit pyruvate carboxylase activity. Additionally, GXDPH can bind to labeled conjugate and prevent enzyme inhibition. Furthermore, free DPH can compete with DPH-avidin for GXDPH binding sites and, the sensitivity of the assay for DPH is within therapeutic levels of 2–30 μg per ml.

EXAMPLE 4

Homogeneous Binding Assay for Lidocaine Fifty microliters (1.1 μg) of pyruvate carboxylase (P.C.), prepared as described in part A of Example 1, was diluted with 25 μl of monoclonal antibody to lidocaine (#43 Kall), 100 μg of lidocaine-avidin conjugate (Lido-avidin) 100 μg, prepared as described in part C of Example 1, and 25 μl of lidocaine containing various μg amounts of lidocaine to a volume of 200 μl and then diluted to 1.0 ml with enzyme substrates as indicated in Table 2. All assay components were pre-equilibrated to 37° C. in a 37° C. water bath and added to a preheated, 37° C. cuvette. The rate or change in absorbance at 412 nm per minute (ΔA) was measured. The rate (ΔA) was subtracted from the rate of the control (ΔA°) containing all reaction components except lidocaine.

TABLE 2

| Rxn No. | P.C. (1.1 μg) | Lido-Avidin (100 μg) | #43 Kall (25 μl) | Lido-caine (μg) | ΔA | (ΔA°-ΔA) × 100 |
|---|---|---|---|---|---|---|
| 1 | + | + | — | — | 0.0616 | — |
| 2 | + | + | + | — | 0.1531 | 0 |
| 3 | + | + | + | 0.0312 | 0.1457 | 0.46 |
| 4 | + | + | + | 0.125 | 0.1400 | 1.31 |
| 5 | + | + | + | 0.25 | 0.1391 | 1.40 |
| 6 | + | + | + | 0.50 | 0.1234 | 2.97 |
| 7 | + | + | + | 1.00 | 0.1175 | 3.56 |
| 8 | + | + | + | 2.00 | 0.1098 | 4.33 |

The results in Table 2 indicate that lidocaine can be conjugated to avidin to form a labeled conjugate (lido-avidin) without destroying avidin's ability to inhibit pyruvate carboxylase activity. Additionally, lidocaine-specific binding component (monoclonal antibody #43 Kall) can bind to labeled conjugate and prevent enzyme inhibition. Furthermore, free lidocaine can compete with lido-avidin for antibody binding sites.

EXAMPLE 5

Homogeneous Binding Assay for Theophylline

Fifty microliters (1.1 μg) of pyruvate carboxylase (P.C.), prepared as described in part A of Example 1, was diluted with 25 μl of rabbit anti-theophylline antibody (RXTh), 100 μl (50 μg) of theophylline-avidin conjugate, (Theo-avidin), prepared as described in part C of Example 1, and 25 μl of theophylline (Theo) containing various μg amounts of theophylline, to a volume of 200 μl and then diluted to 1.0 ml with enzyme substrates as indicated in Table 3. All assay components were pre-equilibrated to 37° C. in a 37° C. water bath and added to a preheated, 37° C. cuvette. The rate or change in absorbance at 412 nm per minute (ΔA) was measured. The rate (ΔA) was subtracted from the rate of the control (ΔA°) containing all reaction components except theophylline.

TABLE

| Rxn No. | P.C. (1.1 μl) | Theo.-Avidin | RxTh (50 μg) | Theo. (25 μl) | ΔA | (ΔA°-ΔA) (μg) / ΔA × 100 |
|---|---|---|---|---|---|---|
| 1 | + | + | — | — | 0.0531 | — |
| 2 | + | + | + | — | 0.1550 | 0 |
| 3 | + | + | + | 0.15 | 0.1573 | −0.20 |
| 4 | + | + | + | 0.63 | 0.1415 | 1.35 |
| 5 | + | + | + | 2.5 | 0.1323 | 2.27 |

The results in Table 3 indicate that theophylline (Theo.) can be conjugated to avidin to form a labeled conjugate (Theo.-avidin) without destroying avidin's ability to inhibit pyruvate carboxylase (P.C.) activity. Additionally, theophylline-specific binding component (RxTh) can bind to labeled conjugate and prevent enzyme inhibition. Furthermore, free theophylline can compete with Theo.-avidin for RxTh binding sites.

What is claimed is:

1. A method for quantitating a first ligand in fluid medium suspected of containing said first ligand comprising intermixing with said fluid medium a biotin-containing enzyme, a labeled conjugate comprising avidin coupled to a second ligand said second ligand comprising a substance identical to said first ligand or an analog of said first ligand, appropriate substrate and cofactors for said biotin-containing enzyme, and a ligand-specific binding component, the activity of said enzyme capable of being modulated by said labeled conjugate, said labeled conjugate having the characteristics that when bound by said ligand-specific binding component it is unable to modulate said enzyme; and thereafter determining the amount of said first ligand in said fluid medium by measuring the change in activity of said enzyme.

2. A method according to claim 1 wherein said first ligand is dilantin.

3. A method according to claim 1 wherein said first ligand is theophylline.

4. A method according to claim 1 wherein said first ligand is lidocaine.

5. A method according to claim 1 wherein said fluid medium is human serum.

6. A method according to claim 1 wherein said enzyme is pyruvate carboxylase.

7. A method according to claim 1, wherein said enzyme activity is measured spectrophotometrically.

8. A method according to claim 1 wherein said ligand-specific binding component is ligand-specific antibody.

9. A method according to claim 8 wherein said antibody is polyclonal antibody.

10. A method according to claim 8 wherein said antibody is monoclonal antibody.

11. A method for quantitating a first ligand in a fluid medium suspected of containing said first ligand, comprising the steps of:
  (a) intermixing said fluid medium with reaction components comprising a labeled conjugate comprising avidin conjugated to a second ligand, said second ligand comprising a substance identical to said first ligand or an analog of said first ligand, a ligand-specific binding component capable of specifically binding to said first ligand or to said labeled conjugate, the biotin-containing enzyme pyruvate carboxylase, and an appropriate substrate and cofactors for said enzyme;
  (b) allowing said reaction mixture to incubate at about 20° C. to about 40° C. for a period of about 0 to about 15 minutes;
  (c) thereafter measuring any change in activity of said enzyme; and
  (d) thereafter correlating said change in enzyme activity to the concentration of said first ligand in said fluid medium.

12. A method according to claim 11 wherein the change in activity of said enzyme is measured spectrophotometrically.

13. A method according to claim 11 wherein said fluid medium is human serum.

14. A method according to claim 11 wherein said first ligand is dilantin.

15. A method according to claim 11 wherein said first ligand is theophylline.

16. A method according to claim 11 wherein said first ligand is lidocaine.

17. A method according to claim 11 wherein said ligand-specific binding component is a ligand-specific antibody.

18. A method according to claim 17 wherein said antibody is a polyclonal antibody.

19. A method according to claim 17 wherein said antibody is a monoclonal antibody.

20. A composition useful in the method for quantitating a first ligand in a fluid medium employing a competitive immunoassay technique, a ligand specific binding component capable of specifically binding to said first ligand, enzyme modulators, and monitoring enzymes, comprising a substance identical to said first ligand or an analog of said first ligand conjugated to avidin to form a labeled conjugate.

21. A composition according to claim 20 wherein said ligand is dilantin.

22. A composition according to claim 20 wherein said ligand is theophylline.

23. A composition according to claim 20 wherein said ligand is lidocaine.

24. A composition according to claim 20 wherein said labeled conjugate can inhibit the activity of a biotin-containing enzyme.

25. A composition according to claim 20 wherein said enzyme is pyruvate carboxylase.

26. A composition according to claim 20 wherein the ratio of said substance to said enzyme modulator in said labeled conjugate is no less than about 1 and no more than about 10.

* * * * *